(12) United States Patent
Giorno

(10) Patent No.: US 10,543,029 B2
(45) Date of Patent: *Jan. 28, 2020

(54) SELF-CLEARING SELF-CUTTING IMPLANT

(71) Applicant: Intra-Lock International, Inc., Boca Raton, FL (US)

(72) Inventor: Thierry Giorno, Boca Raton, FL (US)

(73) Assignee: INTRA-LOCK INTERNATIONAL, INC., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/720,383

(22) Filed: Sep. 29, 2017

(65) Prior Publication Data

US 2018/0078297 A1    Mar. 22, 2018

Related U.S. Application Data

(60) Division of application No. 13/087,454, filed on Apr. 15, 2011, now Pat. No. 9,848,927, which is a continuation-in-part of application No. 12/694,055, filed on Jan. 26, 2010, now Pat. No. 9,707,059.

(60) Provisional application No. 61/390,367, filed on Oct. 6, 2010, provisional application No. 61/147,630, filed on Jan. 27, 2009.

(51) Int. Cl.
*A61B 17/86* (2006.01)
*A61C 8/00* (2006.01)
*H04R 25/00* (2006.01)

(52) U.S. Cl.
CPC .......... *A61B 17/863* (2013.01); *A61C 8/0022* (2013.01); *H04R 25/606* (2013.01); *A61B 17/8605* (2013.01); *A61B 17/8625* (2013.01)

(58) Field of Classification Search
CPC ....... A61C 8/005; A61C 8/006; A61C 8/0022; A61C 8/0024; A61C 8/0025; A61C 8/0069; A61C 8/0089; B23G 2210/28; B23G 2240/08; A61F 2220/0016
USPC ................................ 433/172–174, 215, 225
See application file for complete search history.

(56) References Cited

U.S. PATENT DOCUMENTS

| 2,232,336 | A |   | 2/1941  | Meersteiner |
|-----------|---|---|---------|-------------|
| 4,406,623 | A | * | 9/1983  | Grafelmann ......... A61C 8/0022 433/174 |
| 4,697,969 | A | * | 10/1987 | Sparkes .............. F16B 25/0015 411/387.7 |
| 4,863,383 | A | * | 9/1989  | Grafelmann ....... A61B 17/8625 433/174 |
| 5,273,383 | A |   | 12/1993 | Hughes |
| 5,318,393 | A |   | 6/1994  | Yamada |
| 5,427,526 | A |   | 6/1995  | Fernandes |
| 5,676,545 | A |   | 10/1997 | Jones |
| 5,702,445 | A | * | 12/1997 | Brånemark ........ A61B 17/8625 411/387.3 |

(Continued)

FOREIGN PATENT DOCUMENTS

| GB | 2473482 A1 * | 3/2011 |
| WO | 2010021478 A2 | 2/2010 |
| WO | 2011027338 A1 | 3/2011 |

*Primary Examiner* — Wade Miles
*Assistant Examiner* — Matthew P Saunders
(74) *Attorney, Agent, or Firm* — Reising Ethington P.C.

(57) ABSTRACT

The invention relates to methods of stabilizing bone implants, including inserting a self-tapping implant having at least two helical grooves running in opposite directions around the implant.

4 Claims, 7 Drawing Sheets

(56) References Cited

U.S. PATENT DOCUMENTS

| | | | | |
|---|---|---|---|---|
| 5,759,003 A * | 6/1998 | Greenway | ............ | F16B 25/0015 |
| | | | | 411/399 |
| 5,816,812 A * | 10/1998 | Kownacki | ............ | A61C 8/0022 |
| | | | | 433/174 |
| 5,984,681 A | 11/1999 | Huang | | |
| 6,102,703 A * | 8/2000 | Day | .................... | A61C 8/0006 |
| | | | | 433/173 |
| 6,273,722 B1 * | 8/2001 | Phillips | ................ | A61C 8/0018 |
| | | | | 433/173 |
| 6,319,254 B1 * | 11/2001 | Giet | .................... | A61B 17/863 |
| | | | | 606/104 |
| 6,604,945 B1 * | 8/2003 | Jones | ....................... | A61C 8/00 |
| | | | | 433/173 |
| 7,832,971 B2 * | 11/2010 | Mair | ...................... | F16B 39/30 |
| | | | | 411/418 |
| 9,848,927 B2 * | 12/2017 | Giorno | ................ | H04R 25/606 |
| 9,901,379 B2 * | 2/2018 | Reed | .................. | A61B 17/8625 |
| 2003/0165796 A1 * | 9/2003 | Carmichael | .......... | A61C 8/0022 |
| | | | | 433/174 |
| 2004/0121289 A1 * | 6/2004 | Miller | ................. | A61C 8/0022 |
| | | | | 433/174 |
| 2006/0127193 A1 | 6/2006 | Akaki et al. | | |
| 2008/0118893 A1 | 5/2008 | Armellini et al. | | |
| 2008/0261175 A1 * | 10/2008 | Hurson | ................ | A61C 8/0022 |
| | | | | 433/173 |
| 2009/0220914 A1 | 9/2009 | Gershenzon | | |
| 2010/0190138 A1 * | 7/2010 | Giorno | ................ | A61B 17/863 |
| | | | | 433/174 |
| 2010/0240010 A1 * | 9/2010 | Holmstrom | .......... | A61C 8/0022 |
| | | | | 433/174 |

* cited by examiner

SELF-CLEARING SELF-CUTTING IMPLANT

RELATED APPLICATIONS

This is a divisional patent application which claims the benefit of priority from U.S. patent application Ser. No. 13/087,454 filed on Apr. 15, 2011, which claims the benefit of priority from U.S. Provisional Patent Application No. 61/390,367 filed on Oct. 6, 2010 and U.S. Provisional Patent Application No. 61/147,630 filed on Jan. 27, 2009, and is a continuation-in-part of U.S. patent application Ser. No. 12/694,055 filed on Jan. 26, 2010, which claims the benefit of priority from U.S. Provisional Patent Application No. 61/147,630 filed on Jan. 27, 2009.

FIELD OF INVENTION

The invention relates to bone implants, namely screw-type implants and, more particularly, to a self-tapping dental implant having at least two helical grooves running in opposite directions around the implant. Implants of the present design are easier to insert and are less prone to micromotion than other known implants in the art.

BACKGROUND OF THE INVENTION

It has been discovered that micromotion, movement of an implant relative to the bone it is implanted in, can induce bone absorption around the implant and lead to failure. See Trisi, et al, *Implant micromotion is related to peak insertion torque and bone density*. Clin. Oral. Impl res, 20 (2009) pp 467-71. This movement is believed to destroy the new cells forming in the gap between the bone and implant. In which event, the tendency is for the bone to resorb around the implant to provide a perceived need for clearance. This leads to weakening and potential failure of the implant. To reduce failure, there is a need for an implant which has very high initial stability. To maximize success of dental implants, the micromotion should not exceed 50-100 μm at the implant/bone interface. Pillar, et al., Clin Orthop Relat Res. 1986 July; (208):108-13.

Implants which are designed for a tight fit in the bone generally require significantly more torque to insert.

Implants for insertion into living bone, including screw type implants are widely used and are well known in the art. Such implants may be used in dentistry or orthopedics. The screw tapping implants generally fall into the category of self-tapping implants and non-self-tapping implants. Non-self-tapping implants are merely threaded and are screwed into the bone after it is separately drilled and tapped. Self-tapping implants contain cutting threads analogous to those in a metal tap which cut threads into the bone when inserted in a drilled hole that is smaller than the self-tapping implant diameter. The basic structure of both types of implants comprise a generally cylindrical main body that has a set of external screw threads on the outer surface which engage with threads cut into the bone. The engagement of the threads provides for initial stabilization for the implant. With both types of implants, long term stability is provided by growth of new bone around the implant. A non-self-tapping implant is usually tapered at the end which is inserted into the bone. The other end of both implants contains a means for attaching a dental prosthesis such as a tooth and is often threaded to facilitate attachment of the prosthesis.

Self-tapping implants usually contain a more pronounced taper at the end of the implant on which the cutting threads of the tap portion of the implant are disposed.

Self-tapping devices of the prior art suffer from a number of drawbacks. The thread cutting abilities of present devices are limited due to the thickness of the threads which creates large amounts of bone chips as part of the cutting process. Current designs are unable to effectively clear these bone chips from the hole. Many devices contain flutes which are substantially parallel to the body of the implant and adjacent to cutting surfaces to aid in clearing bone. The collection of chips results in an increase in the torque required to seat a self-tapping implant. The increase in torque adds to patient discomfort and may also lead to breakage of the threads cut in the bone. The inability of the implant to clear debris can also prevent a surgeon from properly seating an implant. The seating and insertion torque problems increase as the length of the implant increases.

Self-tapping implants of the present invention are also ideally suited for osseointegrated hearing aids. Designs in the art suffer from slow or weak osseointegration. Movement of the implant further contributes to resorption of bone in the vicinity of the implant. Existing implants also get loose due to mechanical loading on the implant.

The art contains examples of implant designs having grooves within the cutting surfaces for removing debris.

Published United States patent application US20080187886A1 discloses a self-tapping dental implant having a vertical groove for collecting debris.

Published United States patent application US20080160483A1 discloses a self-tapping implant having a vertical groove for collecting debris.

Published United States patent application US20080131840A1 discloses a self-tapping implant having a groove for holding debris.

Published United States patent application US20080081316A1 discloses a self-tapping implant having a vertical groove for containing debris.

Published United States patent application US20080038693A1 discloses a self-tapping implant having a vertical groove for containing debris.

U.S. Pat. No. 7,281,925 and published United States patent application US20080032264A1 disclose a self-tapping implant having a groove cut within and parallel to the self-tapping threads for containing debris.

Published United States patent application US20080014556A1 discloses a self-tapping implant having a groove running with the threads for containing debris.

U.S. Pat. No. 7,273,373 discloses a self-tapping implant having a groove for containing debris and protrusions to aid in anchoring.

Published United States patent application US20070190491A1 discloses a self-tapping implant which is out of round and has breaks in the self-tapping threads for passage of debris.

Published United States patent application US20070099153A1 discloses a self-tapping implant having a substantially vertical groove in the self-tapping threads for passage of debris.

Published United States patent application US20040121289A1 discloses a self-tapping implant having a substantially vertical groove running in an opposite direction to the cutting threads for passage of debris.

U.S. Pat. No. 6,604,945 discloses a self-tapping implant having a substantially vertical groove running for passage of debris.

Published United States patent application US20020102518A1 discloses an implant having a vertical groove for passage of debris.

U.S. Pat. No. 6,273,722 discloses an implant with helices running in opposite directions. However, this is not a self-tapping implant.

U.S. Pat. No. 5,984,681 discloses a self-tapping implant having open threads and a separate anchor.

U.S. Pat. No. 5,871,356 discloses an implant having vertical grooves for the passage of debris.

U.S. Pat. No. 5,601,429 discloses an implant having grooves for clearing debris running in the same direction as the cutting grooves.

U.S. Pat. No. 4,498,461 discloses an osseointegrated hearing aid.

U.S. Pat. No. 7,116,794 discloses an implant for anchoring a hearing aid.

It has been discovered that micromotion, movement of an implant relative to the bone it is implanted in, can induce bone absorption around the implant and lead to failure. See Trisi, et al, *Implant micromotion is related to peak insertion torque and bone density*. Clin. Oral. Impl res, 20 (2009) pp 467-71. To reduce failure, there is a need for an implant which has very high initial stability. However, implants which are designed for a tight fit in the bone generally require significantly more torque to insert. Despite the above examples, there is still a need in the art for a self-threading implant which is easy to install yet offers acceptable holding power.

OBJECTIVE OF THE INVENTION

It is an objective of this invention to provide an improved self-tapping implant having reduced torque for insertion and an increased load bearing surface at the time of insertion.

It is an objective of the invention to provide an improved self-tapping implant having reduced insertion torque and improved stability for use in anchoring dental devices to bone.

It is an objective of the invention to provide an improved self-tapping implant having reduced insertion torque and improved stability for use in anchoring orthopedic devices to bone.

It is an objective of the invention to provide an improved self-tapping implant having reduced insertion torque and improved stability for use in anchoring osseointegrated hearing aids to bone.

SUMMARY OF THE INVENTION

The present invention comprises a self-tapping implant which requires substantially less torque to install than a traditional self-tapping implant having full screw threads. The reduction in effort is achieved by the inclusion of at least one cutting surface on each rotation of the thread and by including a spiral groove which runs in an opposite direction to the threads. This enables the implant of the present invention to corkscrew into an opening instead of cutting course threads.

Implant designs of the present invention generate significantly less bone debris that the "classic tap cutting grooves". In the present invention, debris, are evenly distributed across the implant body length, rather than "collected" and compressed into either the grooves of the tap or the bottom of the hole in which the implant is being inserted.

According to one embodiment the implant comprises a substantially cylindrical body 1 having a proximal end 2 and a distal end 3. The body contains at least one external helical thread 9 which runs from the distal end 3 to the proximal end 2. The helical thread 9 may be right or left handed and contains at least one cutting edge 6 for each turn of the cutting head. The implant further comprises a second helix 10 running in the opposite direction of the helical thread.

Implants of the present design can be used in dental, surgical, hearing aid applications or any application where a stable support is required in bone.

An unexpected benefit of the design of the present invention is the reduction of micromotion.

DETAILED DESCRIPTION OF THE INVENTION

The present invention comprises a self-tapping implant which requires substantially less torque to install than devices currently in use, yet has significantly reduced micromotion immediately upon insertion. The reduction in effort is achieved by the inclusion of at least one cutting surface on each rotation of the thread about the body of the implant and by including a spiral groove which runs in an opposite direction to the threads. This enables the implant of the present invention to corkscrew into an opening instead of cutting course threads as is done in the art.

Figure 1:
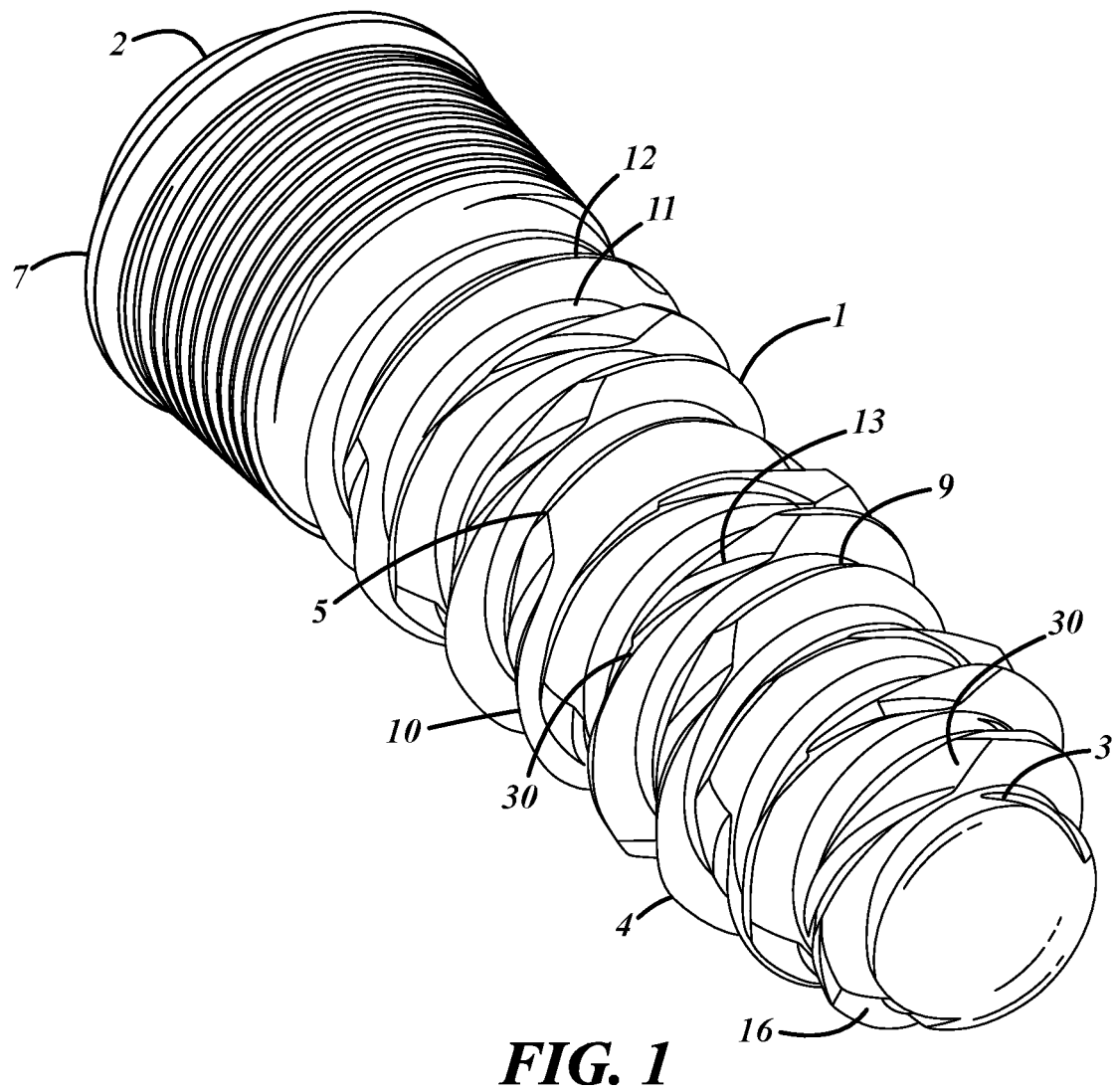
FIG. 1 is a perspective view of a dental implant according to one embodiment.
Figure 2:
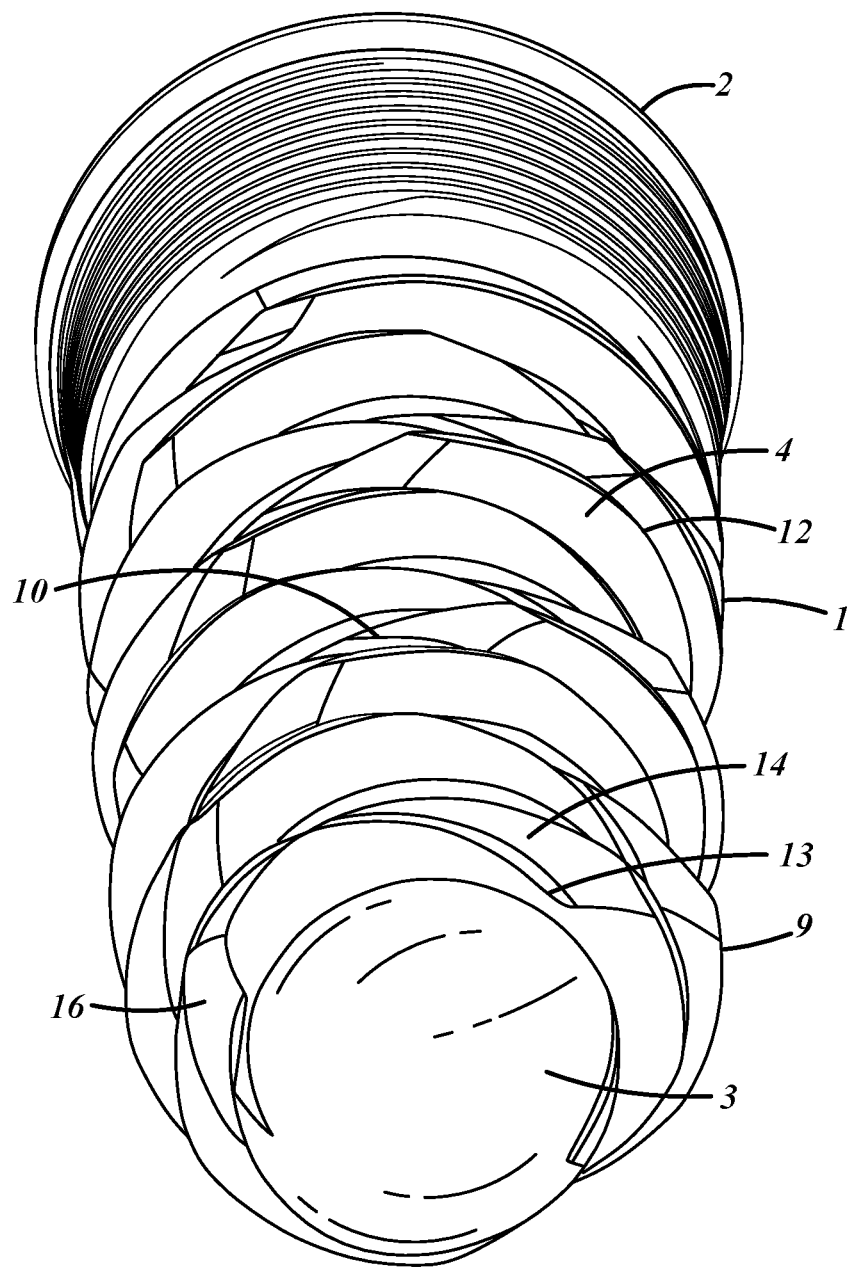
FIG. 2 is a distal end view of a dental implant according to one embodiment.
Figure 3:
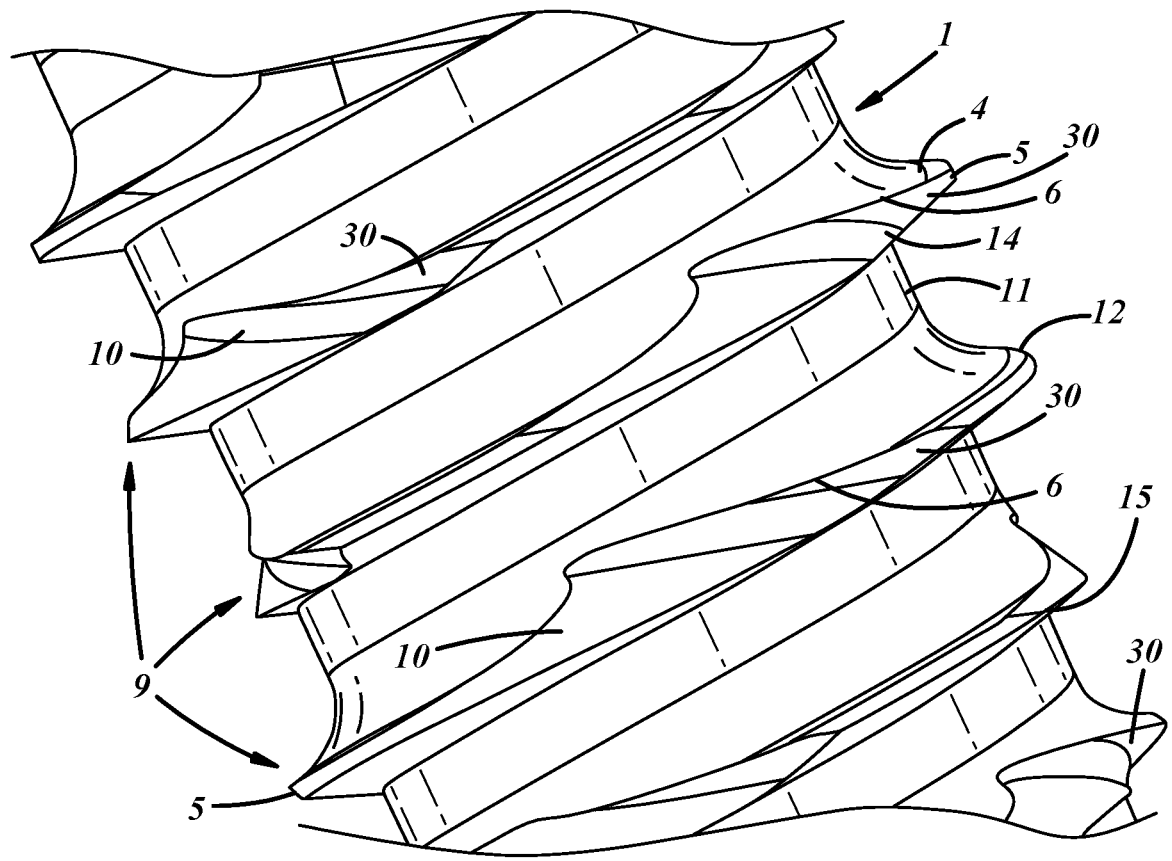
FIG. 3 is an expanded side view of the implant in FIGS. 1 and 2.
Figure 4:
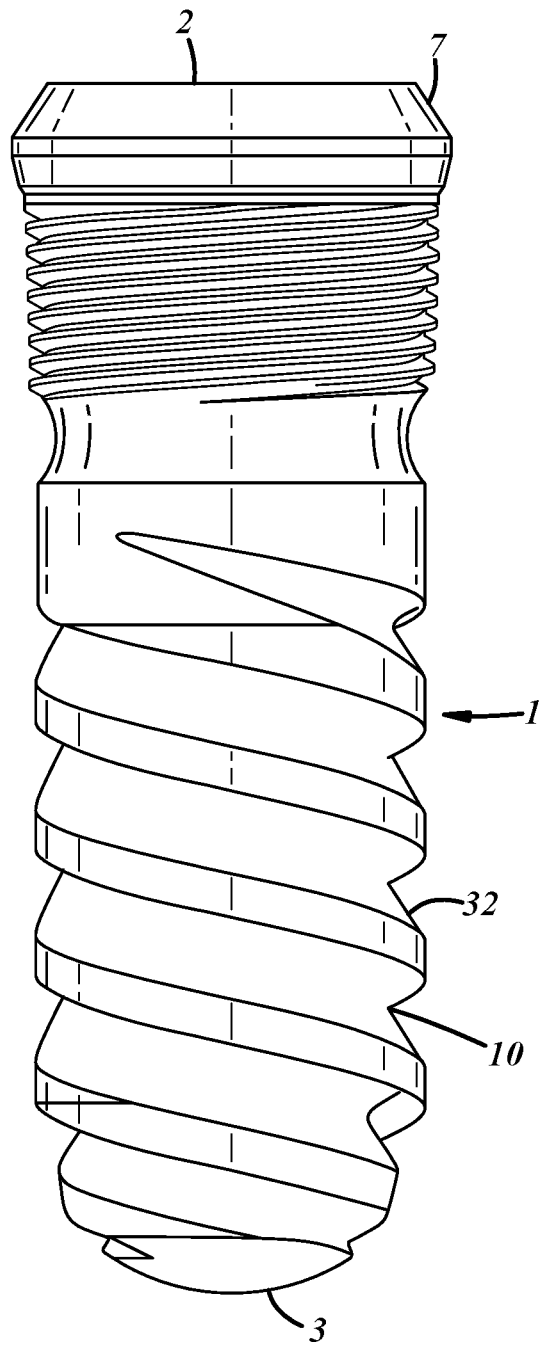
FIG. 4 is a side view showing a secondary helix.

Referring to FIGS. 1-3, according to one dental implant embodiment, the implant comprises a substantially cylindrical body 1 having a proximal end 2 and a distal end 3. The proximal end contains a prosthetic platform 7 onto which a prosthesis will be fitted. The body contains at least one external helical thread 9 which runs from the distal end 3 to the proximal end 2. The helical thread 9 may be right or left handed and contains at least one cutting edge 6 for each turn of the cutting head. The implant further comprises a second helix 10 running in the opposite direction of the helical thread. The second helix 10 is cut at approximately the same depth as the external helical thread 9. The second helix can be seen more clearly in FIG. 4 in which the helical thread 9 has been omitted for clarity.

The helical thread 9 is further comprised of an inner, or minor, diameter 11 and an outer, or major, diameter 12. The outer diameter 12 forms a ridge 4 having a plateau 5 on the outermost thread surfaces which engages with the bone during insertion. It is preferred that the plateau 5 be as narrow as possible subject to the structural limitations of the material comprising the implant. Thinner diameters allow for smaller pilot holes, easier drilling and reduce the torque required for insertion. Larger plateaus may be required for softer bone.

The thread pitch 15 is not critical to the invention and may be increased or decreased depending on the mechanical needs for the application. Thread pitch can be constant or variable.

The helical thread 9 comprises a recess 13 and a beveled surface 14. The angle of the bevel is not critical but should be as narrow as possible to facilitate cutting into the bone, but not so narrow that the structural integrity of the cutting surface and thread is comprised.

The cutting edge 6 is formed by cutting the second helix 10 into the body of the implant and is contiguous with the helical thread 9. In a preferred embodiment, the thread 9 has a chamfer 30 adjacent the cutting edge. The chamfer 30 makes contact with the bone following the cutting edge 6. The second helix, 10 in addition to creating the cutting edge 6, also serves to assist in clearing bone debris created by the cutting edge.

The main body 1 may be straight or tapered, with a straight body being most preferred. When the main body it is straight is preferred that the initial turn of the helix 16 be of a smaller diameter than the rest of the main body 1 to facilitate easy insertion into the pilot hole.

In yet another embodiment a secondary thread (not shown) may be included inside the helical thread 9.

Figure 5:
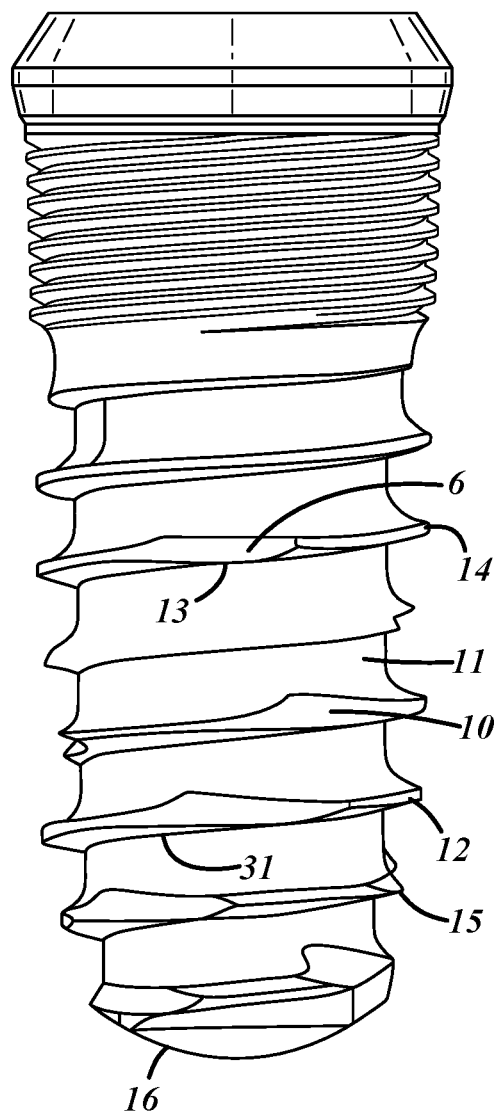
FIG. 5 is a side view showing the details for a particular embodiment of a dental implant.

FIG. 5 shows an embodiment in which the implant is 4 mm in length and has an outer diameter 12 of 0.1540 cm and an inner diameter 11 of 0.12 cm. The distance between the leading edges of the thread 9 is 0.354 cm and each thread has a 15° undercut on the bottom side and a cut having a radius of 0.015 cm on the top side. The secondary helix 10 is cut at a depth of 0.130 cm. The top of the secondary helix forms the cutting edge 6 and is cut at a 60° angle which results in the cutting edge being raked such that the leading edge is raked away from the direction of the thread 9.

One of skill in the art will appreciate that the surface of the implant can be further processed to aid in growth of new bone around it. Such processing can include the use of coatings or modifying the surface textures of the implant as is known in the art.

The prosthetic platform may be structured to accommodate any form of implant. It can comprise internal threads (not shown) which are inside the body of the implant or external threads (not shown) or comprise any type of stud or ball upon which a prosthesis can be mounted. The thread pitch is not critical and may be selected for the application. In yet other embodiments, the implant may contain surfaces suitable for bonding the prosthesis to the implant.

The implant of the present invention is used in a conventional manner. The dentist or surgeon will drill a pilot hole for the implant. The implant is attached to an insertion tool and turned into the pilot hole. Upon turning, the cutting edge 6 will cut a groove into the bone into which the helical thread 9 will follow. Because cutting edge 6 has a sharp edge leading into a narrow plateau on the helical thread 9, less bone debris is generated. This debris is pushed towards the proximal end of the body through the second helical groove 10. This movement of debris keeps the pilot hole relatively free from debris thereby preventing debris from filling the pilot hole or binding or jamming the implant. This reduces incidences of the implant prematurely bottoming out in the pilot hole because of debris filling the hole and reduces the debris caught in the helical groove thereby reducing friction on the cutting surfaces which reduces the torque required for insertion.

Manufacturing

Implants of the present invention can be manufactured from any structural material suitable for dental implants, including but not limited to stainless steels, titanium, ceramics, polymers and any other material with appropriate mechanical characteristics which is biocompatible. Titanium is most preferred. Implants of the present invention can be readily manufactured using a modern lathe capable of cutting screw threads. The unfinished stock is mounted in the lathe at the proximal end. The cutting blade of the lathe cuts a helical groove in the stock leaving the desired primary thread. The direction of rotation is then changed and the desired secondary helical groove is cut across the primary thread thereby creating the cutting surfaces. The shape of the helices is determined by the cutting head on the lathe and different cutting heads can be used to create different helices. It will be appreciated that both straight and tapered implants can be created in this manner.

Alternatively, depending on the manufacturing materials, the implant can be formed by passing the stock comprising the body through one or more cutting dies as is known in the art or by the use of molds or forging. For implants made of plastics, ceramics or polymers, molding is the preferred method of manufacture.

As long as the properties of the implant materials are taken into account any thread pitch, thread thickness and cutting edge are possible up the point where the material is too thin to support the load placed on it. Threads and cutting edges that are too thin may break under higher torques or distort during insertion.

Reduction of Insertion Torque

Experiments were performed comparing the insertion of the implant of the present invention with an equal diameter implant using classic cutting flukes. In the test protocol, high density polyurethane was used to simulate bone. A block of polyurethane was secured to a work station and 3.2 mm holes drilled in the block. The implants were then inserted using a digital torque wrench (Tohnichi, Japan). The insertion torque was recorded in Newton centimeters after each complete turn and the data recorded. These data are shown in Tables 1 and 2 below.

TABLE 1

Insertion Torque for Improved Cutting Flukes
Insertion torque for implant having improved cutting flutes), 0.125 (3.2 mm) hole

| # of turns | Sample 1 | Sample 2 | Sample 3 | Sample 4 | Sample 5 | Average |
|---|---|---|---|---|---|---|
| 1 | | 6 | 6 | 6 | 6 | 6 |
| 2 | | 10 | 10 | 9 | 6 | 8.75 |
| 3 | | 12 | 12 | 12 | 9 | 11.25 |
| 4 | | 13 | 14 | 15 | 10 | 13 |
| 5 | | 15 | 16 | 17 | 12 | 15 |
| 6 | | 16 | 18 | 19 | 14 | 16.75 |
| 7 | | 17 | 19 | 22 | 16 | 18.5 |
| 8 | | 20 | 21 | 23 | 19 | 20.75 |
| 9 | | 22 | 23 | 23 | 20 | 22 |
| 10 | | 26 | 26 | 26 | 22 | 25 |
| 11 | | 27 | 28 | 29 | 23 | 26.75 |
| 12 | | 31 | 28 | 31 | 29 | 29.75 |
| 13 | | 42 | 45 | 47 | 45 | 44.75 |

TABLE 2

Insertion Torque for Classic Cutting Flutes
Insertion torque for implant w/ classic cutting flutes 0.125 (3.2 mm) hole

| #of turns | Test 1 | Test 2 | Test 3 | Test 4 | Average |
|---|---|---|---|---|---|
| 1 | 4 | 6 | 5 | 7 | 5.5 |
| 2 | 8 | 10 | 9 | 9 | 9 |
| 3 | 10 | 11 | 11 | 10 | 10.5 |
| 4 | 12 | 13 | 14 | 13 | 13 |
| 5 | 16 | 18 | 15 | 16 | 16.25 |
| 6 | 18 | 19 | 19 | 19 | 18.75 |
| 7 | 22 | 22 | 24 | 23 | 22.75 |
| 8 | 25 | 27 | 29 | 27 | 27 |
| 9 | 32 | 33 | 35 | 32 | 33 |
| 10 | 37 | 41 | 42 | 38 | 39.5 |
| 11 | 44 | 49 | 51 | 47 | 47.75 |
| 12 | 54 | 62 | 65 | 59 | 60 |
| 13 | 67 | 78 | 80 | 77 | 75.5 |

Figure 6:
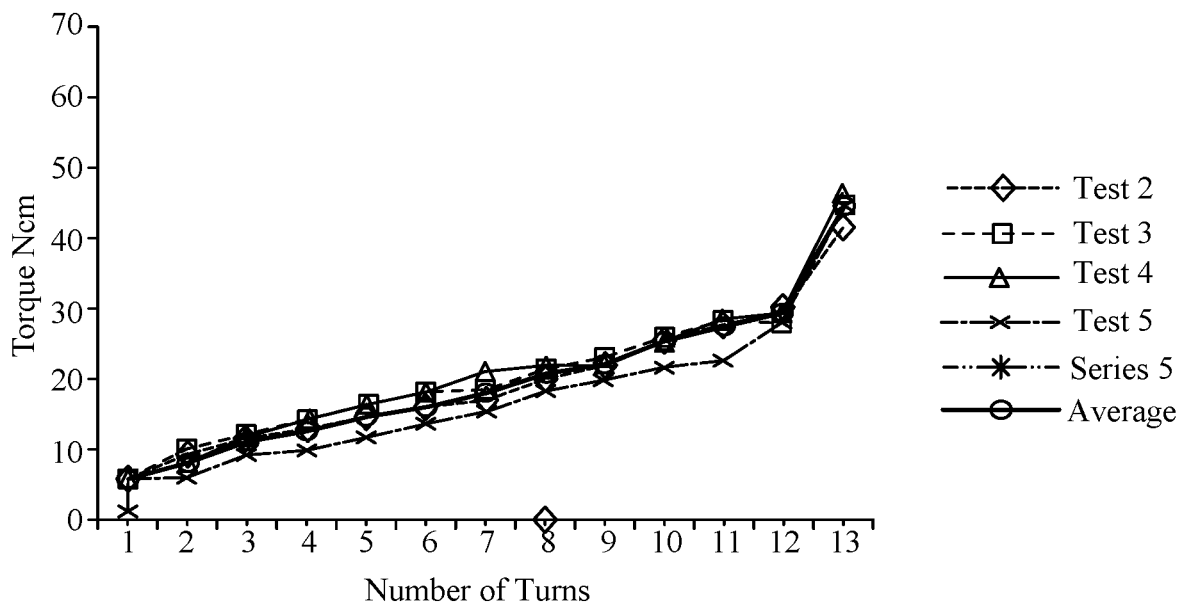
FIG. 6 is a graph of insertion torque for a dental implant according to one embodiment.
Figure 7:
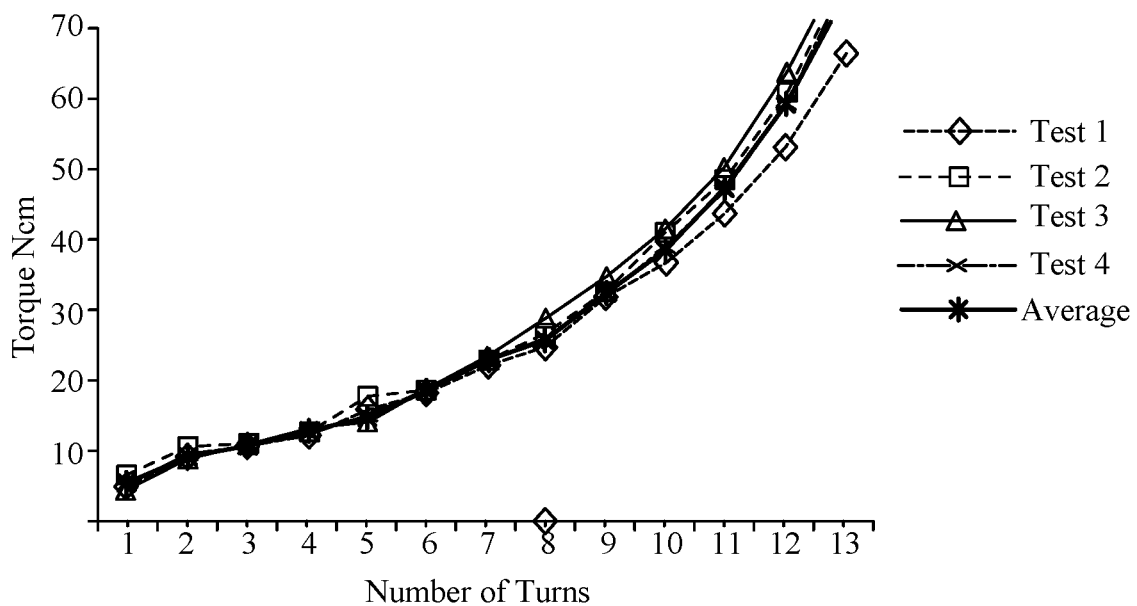
FIG. 7 is a graph of insertion torque for a dental implant using prior art designs.

The data in Tables 1 and 2 shows that the insertion torque of the implant of the present invention is comparable to the insertion torque of the classic design for shallower insertion depths. However, as depth of insertion increases, the classic implant design requires significantly more torque to insert in contrast to the implant of the present invention. These same data are graphed in FIGS. 6 and 7.

Figure 8:
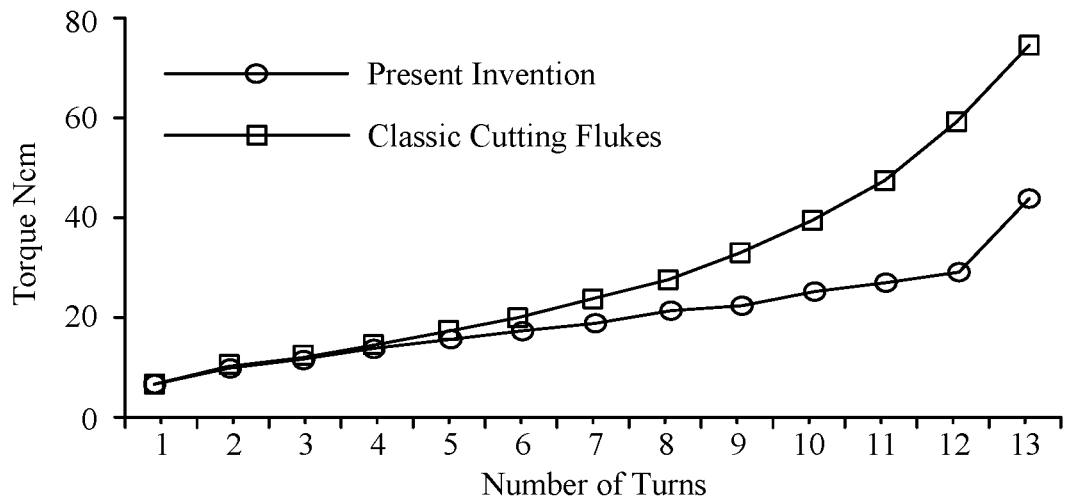
FIG. 8 is a graph comparing the average insertion torque of the present invention to a prior art design.

Referring to FIG. 8 which is a line graph comparing the average torques recorded for each turn in Tables 1 and 2 above. FIG. 8 shows that the cutting flukes of the present invention require substantially less torque as the implant is turned deeper into the socket. The present invention only required an average of 16.75 Ncm of torque during insertion of turn 8 compared with 27 Ncm of torque for the version of the implant having classic cutting flukes. The results are even more dramatic at 13 turns in which the present invention only required 44.75 Ncm of torque compared to 75.5 Ncm of torque for the version of the implant having classic cutting flukes. The present invention will allow easier insertion by a surgeon and reduce the discomfort felt by the patient.

A second set of experiments were performed to further test insertion torque. Table 3 below shows the insertion torque for a conventional implant.

TABLE 3

Insertion Torque for Present Invention

| | Implant Number/Torque (N cm) | | | | | | | | | | | | Mean | Std. |
|---|---|---|---|---|---|---|---|---|---|---|---|---|---|---|
| Turns | 1 | 2 | 3 | 4 | 5 | 6 | 7 | 8 | 9 | 10 | 11 | 12 | Torque | Dev |
| 1 | 1 | 1.8 | 2.4 | 1 | 2.6 | 1 | 1 | 1.4 | 1.4 | 3.6 | 2.4 | 5.6 | 2.1 | 1.376 |
| 2 | 3.2 | 2 | 3.8 | 1.2 | 10.2 | 1.4 | 1.2 | 8 | 6 | 3.8 | 2.4 | 13.2 | 4.7 | 3.895 |
| 3 | 3.8 | 2.6 | 17.4 | 1.6 | 17.4 | 5.2 | 1.6 | 16.8 | 15.6 | 4.4 | 12.4 | 22.4 | 8.37 | 7.599 |
| 4 | 4.4 | 3.7 | 42.2 | 5.2 | 31.6 | 8.4 | 6.6 | 27.2 | 23.8 | 9.4 | 21 | 28.2 | 17.6 | 12.97 |
| 5 | 5.8 | 5.6 | 48 | 6.4 | 35.4 | 11.6 | 13.4 | 39.6 | 37 | 19.4 | 36.4 | 44.4 | 25.25 | 16.34 |
| 6 | 6.8 | 15.8 | 64.8 | 7.2 | 41 | 18.2 | 20.4 | 55.4 | 49.4 | 25.2 | 47.8 | 56 | 34 | 20.6 |
| 7 | 13.4 | 22.8 | 82.6 | 8 | 54.8 | 24.4 | 26.6 | 59.2 | 49.4 | 40 | 49.2 | 72 | 41.9 | 23.37 |
| 8 | 20.4 | 37.8 | 83.8 | 9.2 | 70.4 | 42.8 | 29.4 | 60 | 62.6 | 54 | 54.4 | 88 | 51.1 | 24.21 |
| 9 | 29.2 | 49.2 | 91.8 | 11.1 | 92.6 | 58.2 | 47.4 | 74.8 | 80.2 | 67.2 | 66.4 | 101.2 | 61.1 | 26.81 |
| 10 | 35 | 63.8 | 113.2 | 12.6 | 101.2 | 64.6 | 58.4 | 94.2 | 98.2 | 79.8 | 84.8 | 126.2 | 77.67 | 32.63 |
| 11 | 43.8 | 78.4 | | 13.2 | 123.4 | 67.2 | 76.6 | 121.2 | 130.8 | 96.2 | 97.8 | | 84.9 | |
| 12 | 59.2 | 90 | | 15.8 | | 84.2 | 76.6 | | | 122.6 | 136.2 | | 83.5 | |
| height (mm) | 3.71 | 3.77 | 3.71. | 3.74 | 3.79 | 3.7 | 3.72 | 3.7 | 3.71 | 3.91 | 3.81 | 3.84 | | |

TABLE 4

Insertion Torque for Fluted implants.

| | Implant Number/Torque (N cm) | | | | | | | | | | | | Mean | Std. |
|---|---|---|---|---|---|---|---|---|---|---|---|---|---|---|
| Turns | 1 | 2 | 3 | 4 | 5 | 6 | 7 | 8 | 9 | 10 | 11 | 12 | Torque | Dev |
| 1 | 10.8 | 9.2 | 7.6 | 8.6 | 9.2 | 8.4 | 9.2 | 9.4 | 7.4 | 6.2 | 6.6 | 7.2 | 8.317 | 1.34 |
| 2 | 13.6 | 18.8 | 13.6 | 15.2 | 14.8 | 19.2 | 18.6 | 16.8 | 15.8 | 12.8 | 18.2 | 17.6 | 16.25 | 2.26 |
| 3 | 22 | 27.6 | 18.2 | 18.6 | 26.8 | 27.8 | 30.6 | 28.6 | 24 | 23.2 | 28.8 | 24.4 | 25.05 | 4.02 |
| 4 | 28.2 | 45 | 26.6 | 26.6 | 29.4 | 40.4 | 45.6 | 42.4 | 34.8 | 38.6 | 41 | 40 | 36.55 | 7.14 |
| 5 | 41.8 | 58.4 | 43.4 | 40.2 | 44.4 | 54.6 | 54.2 | 58 | 45 | 49.8 | 47.4 | 54.2 | 49.28 | 6.43 |
| 6 | 59 | 71.4 | 57.2 | 50.6 | 60.2 | 70.8 | 73.2 | 74.6 | 60.2 | 61 | 59.4 | 69.8 | 63.95 | 7.64 |
| 7 | 85.2 | 78.2 | 78.4 | 70.4 | 84.2 | 94.2 | 93.8 | 92.2 | 81.8 | 81 | 80.2 | 93.8 | 84.45 | 7.63 |
| 8 | 106.4 | 94.2 | 105.4 | 98.8 | 106.8 | 131.8 | 134.2 | 121.2 | 108.6 | 107.2 | 101 | 140.8 | 113 | 15.18 |
| 9 | 132.8 | 120.8 | 129 | 123.8 | 135 | 170.2 | 168.2 | 151.2 | 124.6 | 139.6 | 125 | 152.2 | 139.4 | 17.24 |
| 10 | 159.2 | 145.6 | 158.4 | 156 | 185.2 | 202.4 | 200.4 | 185.2 | 160.2 | 161.2 | 167.4 | 184 | 172.1 | 18.59 |
| height (mm) | 3.62 | 3.56 | 3.6 | 3.71 | 3.72 | 3.72 | 3.66 | 3.6 | 3.66 | 3.86 | 3.83 | 3.88 | | |

Table 5 below shows the insertion torque for a non-fluted implant.

TABLE 5

Insertion Torque for Non-Fluted Implant.

| Turns | Implant Number/Torque (N cm) | | | | | | | | | | | | Mean Torque | STD |
|---|---|---|---|---|---|---|---|---|---|---|---|---|---|---|
| | 1 | 2 | 3 | 4 | 5 | 6 | 7 | 8 | 9 | 10 | 11 | 12 | | |
| 1 | 18.8 | 4.8 | 13.4 | 8.8 | 9.4 | 11.2 | 8.4 | 10.4 | 3.6 | 6.4 | 15.2 | 5.6 | 9.67 | 4.48 |
| 2 | 44.8 | 39.4 | 39 | 39.6 | 24.4 | 39 | 37.4 | 41.2 | 21.8 | 36.2 | 43.8 | 23.8 | 35.87 | 7.95 |
| 3 | 74.6 | 71.8 | 70.2 | 71.4 | 49.2 | 69.8 | 68.6 | 69.8 | 41.6 | 67.6 | 71 | 46.2 | 64.32 | 11.49 |
| 4 | 103.6 | 96.4 | 98.2 | 99.2 | 72.2 | 96.6 | 99 | 98.8 | 59 | 99.4 | 97.2 | 68.2 | 90.65 | 14.98 |
| 5 | 133 | 121.4 | 124 | 131.4 | 101.4 | 126.4 | 125 | 130.4 | 78.6 | 128.4 | 123.2 | 89.2 | 117.7 | 17.90 |
| 6 | 159.6 | 142 | 155.4 | 152.6 | 123.2 | 158.8 | 143.8 | 162.4 | 94.4 | 162.2 | 150.6 | 106.6 | 142.6 | 22.67 |
| 7 | 182.8 | 159.8 | 177.2 | 186.4 | 139.2 | 176.6 | 173.4 | 190.6 | 114.8 | 200.2 | 176.8 | 125.6 | 167 | 26.77 |
| 8 | 198 | 199 | 199.8 | 207.6 | 151.4 | 203 | 198.4 | 200.2 | 126.6 | 213.6 | 204 | 141.8 | 187 | 29.18 |
| 9 | 213.8 | 208.6 | 222.8 | 209.8 | 166.6 | 221.8 | 212 | 221.6 | 157.8 | 232.6 | 218.6 | 176.8 | 205.2 | 24.27 |
| height (mm) | 4.41 | 4.47 | 4.41 | 4.42 | 4.34 | 4.44 | 4.43 | 4.48 | 4.42 | 4.48 | 4.49 | 4.5 | | |

Figure 9:
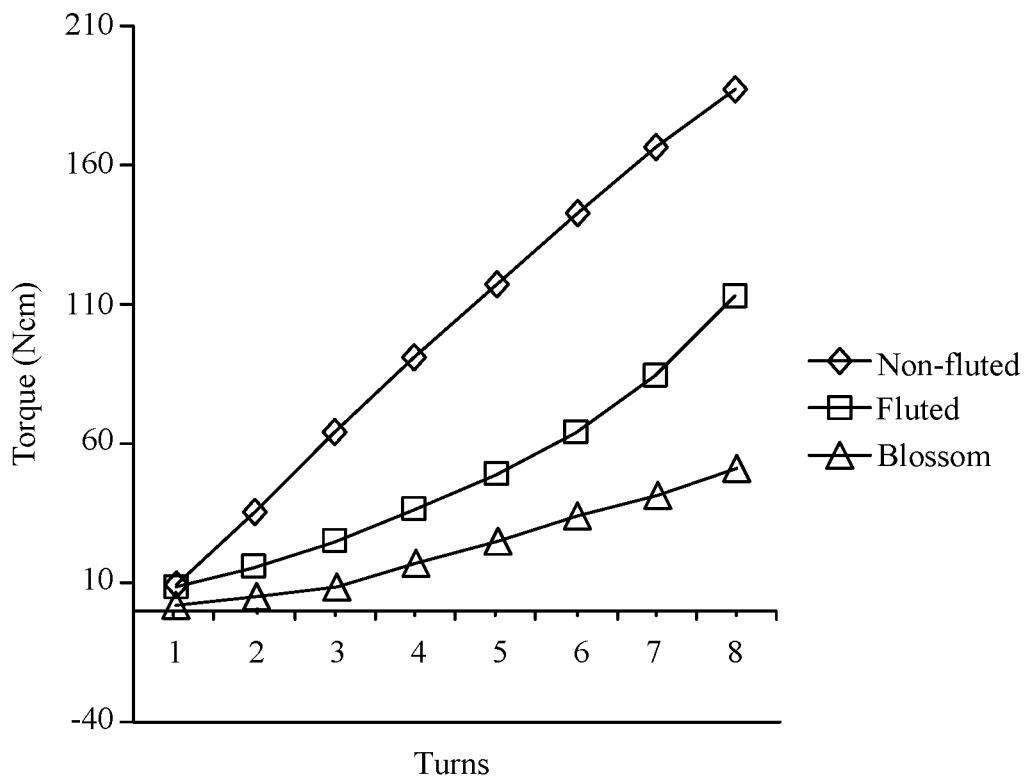
FIG. 9 is a composite line graph comparing the insertion torque for an implant of the present invention with conventional fluted and non-fluted implants

Referring now to FIG. 9 which is a line graph comparing the average insertion torques over 8 turns for implants of the present invention, fluted implants and non-fluted implants. As can be readily seen, the implants of the present design require substantially less torque for insertion. This results in less discomfort to the patient, less effort for the dentist and as show below a more stable implant.

Reduction of Micromotion

Most implants require from 3-6 months to stabilize following implantation before a prosthesis can be installed. This is because the implants are subject to small amounts of motion called micromotion, movement between the bone and the implant, in the range of a few microns to almost a millimeter in bad cases. This is believed to be caused by a number of factors. In many cases, when a hole is drilled, the bore may not be uniformly round and may have voids or protruding portions surround the hole. When an implant is inserted into the bore, it will follow the path of least resistance and will be pushed aside in regions where there is a protrusion in the wall and will follow areas where there is a void in the wall. Conventional implants press upon the walls of the bore more than they cut a thread. The course nature of cutting grooves on conventional implants require sufficiently high torque that they will be pushed aside rather than cut a thread as it follows the path of least resistance. If the implant is not true in the bore, it will have greater motion until bone grows around it and before it can be safely loaded by chewing. Typically, this waiting period is 3-6 months.

Additionally, the areas of bone which are subject to pressure from the implant will initially experience absorption of the bone before new bone is deposited. This results in a loosening of the initial fit of the implant.

Implantation of conventional self-tapping implants is usually spread over 3-6 months. On the initial visit, the bore for the implant will be drilled and the implants placed. The patient must then wait until new bone growth stabilizes the implants at which point the patient returns for installation of any prosthesis. The total chair time for a patient implanted with conventional implants can be between 20-30 hours for implantation of 24 implants with prosthetic teeth. The cost for such a procedure can exceed one hundred thousand dollars and requires multiple visits to the dentist.

Applicant was surprised to learn that the implants of the present design substantially eliminate micromotion and therefore allow immediate loading of the implant. Without being limited to any theory, the reduction of micromotion is believed to result from a combination of factors. First, the sharp cutting surfaces are believed to overcome the forces exerted by protrusions in the bore allowing the implant to be inserted true to the bore. Second, because the implant cuts better grooves, there are fewer regions of high pressure and therefore less bone absorption following implantation.

Patients undergoing treatment with the implant of the present invention can be treated in as few as four to five hours of time in the dental chair. The bores are drilled, the implants inserted and if available, the prosthesis can be attached on the same day if it is available. Potentially, the reduction in time spent in the chair reduces patient costs to about twenty five percent of the cost of conventional implants.

Implant Micromotion Determined by Applied Force

A total of 36 titanium implants representing three categories: an implant of the present invention, a fluted conventional implant and a non-fluted conventional implant, were loaded onto six, 5 cm×5 cm solid, rigid polyurethane foam blocks (Sawbones, Wash., USA) simulating bone with a hardness of D2. Each implant was fitted with a one-piece abutment to allow for the application of a load. Identical abutments were used throughout the procedure. A groove has been machined on each abutment, in order to make sure that the point of application of the force to the crest of the bone is always the same. A customized loading device, consisting of a digital micrometer (Mitutoyo Absolute Digimatic) and digital force gauge (Chantillion E-DFE-025) was used to determine implant micromotion.

The implants were placed in the polyurethane foam blocks utilizing the Tohnichi Digital Torque Gauge. The implants were loaded into the polyurethane block up to the base of the micro-thread. Torque has been recorded after each turn of the implant into the blocks. The abutment was then placed on the implant and secured using an insertion torque of 35 N cm as measured by a TOHNICHI Digital Torque Gauge Model BTGE IOCN.

After the implants were placed, the polyurethane blocks were fixed on a customized loading apparatus for the evaluation of micromovement. The apparatus consisted of a digital force gauge [Chantillion E-DFE-025] vertically fixed onto a frame and, on the opposite side, a digital micrometer [Mitutoyo Absolute Digimatic] that measured the micromotion of the abutment during the load application. The forces were achieved by turning a dial, which controlled the height of the force gauge. This dialed-in force was applied to the abutment via a lever. The micrometer was placed tangent to the crown of the abutment to detect displacement. Loads were tested on each implant starting at 10 N cm and continuing to 100 N cm and measured at 5 N cm increments.

Table 6 below shows the micromovement of an implant of the present invention.

TABLE 6

Micromovement of Implant of Present Invention

| Force | Implant Number/Motion | | | | | | | | | | | | Mean Disp.t | Std |
|---|---|---|---|---|---|---|---|---|---|---|---|---|---|---|
| ((N) | 1 | 2 | 3 | 4 | 5 | 6 | 7 | 8 | 9 | 10 | 11 | 12 | (mm) | Dev |
| 10 | 0.027 | 0.031 | 0.029 | 0.015 | 0.024 | 0.033 | 0.027 | 0.03 | 0.025 | 0.034 | 0.032 | 0.03 | 0.03 | 0.01 |
| 15 | 0.053 | 0.05 | 0.043 | 0.031 | 0.038 | 0.059 | 0.048 | 0.063 | 0.049 | 0.059 | 0.05 | 0.043 | 0.05 | 0.01 |
| 20 | 0.07 | 0.068 | 0.058 | 0.051 | 0.057 | 0.084 | 0.068 | 0.102 | 0.088 | 0.1 | 0.066 | 0.059 | 0.07 | 0.02 |
| 25 | 0.095 | 0.091 | 0.081 | 0.066 | 0.076 | 0.114 | 0.096 | 0.115 | 0.112 | 0.135 | 0.088 | 0.082 | 0.10 | 0.02 |
| 30 | 0.116 | 0.113 | 0.102 | 0.089 | 0.098 | 0.136 | 0.121 | 0.136 | 0.133 | 0.162 | 0.106 | 0.107 | 0.12 | 0.02 |
| 35 | 0.14 | 0.133 | 0.125 | 0.108 | 0.124 | 0.166 | 0.15 | 0.155 | 0.153 | 0.19 | 0.133 | 0.126 | 0.14 | 0.02 |
| 40 | 0.164 | 0.156 | 0.15 | 0.129 | 0.148 | 0.193 | 0.175 | 0.179 | 0.172 | 0.21 | 0.158 | 0.149 | 0.17 | 0.02 |
| 45 | 0.187 | 0.184 | 0.173 | 0.15 | 0.173 | 0.223 | 0.206 | 0.201 | 0.193 | 0.236 | 0.187 | 0.171 | 0.19 | 0.02 |
| 50 | 0.214 | 0.207 | 0.2 | 0.175 | 0.201 | 0.252 | 0.237 | 0.226 | 0.217 | 0.265 | 0.218 | 0.197 | 0.22 | 0.02 |
| 55 | 0.238 | 0.234 | 0.224 | 0.202 | 0.23 | 0.284 | 0.28 | 0.257 | 0.237 | 0.287 | 0.249 | 0.22 | 0.25 | 0.03 |
| 60 | 0.263 | 0.264 | 0.251 | 0.231 | 0.259 | 0.316 | 0.305 | 0.279 | 0.26 | 0.315 | 0.283 | 0.238 | 0.27 | 0.03 |
| 65 | 0.291 | 0.291 | 0.279 | 0.259 | 0.294 | 0.351 | 0.34 | 0.308 | 0.285 | 0.346 | 0.323 | 0.27 | 0.30 | 0.03 |
| 70 | 0.324 | 0.32 | 0.307 | 0.287 | 0.324 | 0.386 | 0.374 | 0.339 | 0.309 | 0.378 | 0.364 | 0.297 | 0.33 | 0.03 |
| 75 | 0.346 | 0.348 | 0.335 | 0.315 | 0.358 | 0.42 | 0.409 | 0.377 | 0.335 | 0.412 | 0.4 | 0.324 | 0.36 | 0.04 |
| 80 | 0.376 | 0.376 | 0.364 | 0.343 | 0.39 | 0.454 | 0.449 | 0.39 | 0.361 | 0.448 | 0.438 | 0.355 | 0.40 | 0.04 |
| 85 | 0.408 | 0.411 | 0.39 | 0.375 | 0.426 | 0.492 | 0.486 | 0.42 | 0.385 | 0.478 | 0.483 | 0.383 | 0.43 | 0.04 |
| 90 | 0.437 | 0.439 | 0.42 | 0.405 | 0.459 | 0.532 | 0.523 | 0.447 | 0.413 | 0.516 | 0.518 | 0.412 | 0.46 | 0.049 |
| 95 | 0.468 | 0.472 | 0.452 | 0.445 | 0.498 | 0.597 | 0.561 | 0.48 | 0.44 | 0.552 | 0.575 | 0.443 | 0.46 | 0.057 |
| 100 | 0.5 | 0.505 | 0.477 | 0.477 | 0.53 | 0.616 | 0.598 | 0.511 | 0.469 | 0.587 | 0.615 | 0.475 | 0.53 | 0.058 |

Table 7 below shows the micromovement of a conventional fluted implant. The mean displacement is higher than in the implants of the present invention.

TABLE 7

Micromovement of a Conventional Fluted Implant

| Force | Implant Number/Motion mm | | | | | | | | | | | | Mean Displ | Std |
|---|---|---|---|---|---|---|---|---|---|---|---|---|---|---|
| ((N) | 1 | 2 | 3 | 4 | 5 | 6 | 7 | 8 | 9 | 10 | 11 | 12 | (mm) | Dev |
| 10 | 0.025 | 0.029 | 0.02 | 0.026 | 0.023 | 0.029 | 0.02 | 0.018 | 0.019 | 0.029 | 0.036 | 0.026 | 0.03 | 0.01 |
| 15 | 0.038 | 0.045 | 0.052 | 0.041 | 0.034 | 0.103 | 0.072 | 0.048 | 0.045 | 0.044 | 0.09 | 0.05 | 0.06 | 0.02 |
| 20 | 0.053 | 0.065 | 0.111 | 0.056 | 0.048 | 0.174 | 0.13 | 0.113 | 0.081 | 0.061 | 0.148 | 0.082 | 0.09 | 0.04 |
| 25 | 0.072 | 0.097 | 0.142 | 0.077 | 0.088 | 0.242 | 0.207 | 0.197 | 0.128 | 0.121 | 0.181 | 0.139 | 0.14 | 0.06 |
| 30 | 0.09 | 0.17 | 0.164 | 0.123 | 0.131 | 0.277 | 0.274 | 0.24 | 0.203 | 0.206 | 0.215 | 0.179 | 0.19 | 0.06 |
| 35 | 0.11 | 0.26 | 0.188 | 0.188 | 0.177 | 0.318 | 0.306 | 0.27 | 0.24 | 0.234 | 0.249 | 0.204 | 0.23 | 0.06 |
| 40 | 0.131 | 0.339 | 0.207 | 0.238 | 0.219 | 0.345 | 0.319 | 0.291 | 0.262 | 0.26 | 0.281 | 0.227 | 0.26 | 0.06 |
| 45 | 0.15 | 0.37 | 0.227 | 0.266 | 0.239 | 0.372 | 0.338 | 0.312 | 0.286 | 0.287 | 0.315 | 0.253 | 0.28 | 0.06 |
| 50 | 0.172 | 0.395 | 0.248 | 0.293 | 0.26 | 0.403 | 0.356 | 0.331 | 0.312 | 0.313 | 0.351 | 0.276 | 0.31 | 0.07 |
| 55 | 0.194 | 0.422 | 0.269 | 0.347 | 0.283 | 0.441 | 0.38 | 0.351 | 0.341 | 0.34 | 0.371 | 0.308 | 0.34 | 0.07 |
| 60 | 0.216 | 0.452 | 0.294 | 0.362 | 0.303 | 0.463 | 0.401 | 0.372 | 0.367 | 0.37 | 0.402 | 0.33 | 0.36 | 0.07 |
| 65 | 0.241 | 0.473 | 0.316 | 0.379 | 0.324 | 0.492 | 0.425 | 0.39 | 0.386 | 0.399 | 0.443 | 0.354 | 0.39 | 0.07 |
| 70 | 0.264 | 0.5 | 0.34 | 0.406 | 0.353 | 0.525 | 0.448 | 0.412 | 0.415 | 0.425 | 0.465 | 0.38 | 0.41 | 0.07 |
| 75 | 0.288 | 0.534 | 0.365 | 0.435 | 0.374 | 0.554 | 0.474 | 0.44 | 0.446 | 0.453 | 0.495 | 0.402 | 0.44 | 0.07 |
| 80 | 0.312 | 0.559 | 0.391 | 0.468 | 0.395 | 0.585 | 0.498 | 0.47 | 0.473 | 0.482 | 0.528 | 0.429 | 0.47 | 0.08 |
| 85 | 0.337 | 0.601 | 0.418 | 0.498 | 0.421 | 0.618 | 0.524 | 0.501 | 0.5 | 0.51 | 0.567 | 0.456 | 0.50 | 0.08 |
| 90 | 0.382 | 0.628 | 0.447 | 0.525 | 0.441 | 0.648 | 0.551 | 0.528 | 0.526 | 0.539 | 0.594 | 0.484 | 0.52 | 0.08 |
| 95 | 0.408 | 0.66 | 0.48 | 0.563 | 0.466 | 0.679 | 0.574 | 0.561 | 0.559 | 0.571 | 0.627 | 0.513 | 0.56 | 0.08 |
| 100 | 0.427 | 0.694 | 0.511 | 0.599 | 0.494 | 0.705 | 0.6 | 0.592 | 0.588 | 0.602 | 0.672 | 0.547 | 0.59 | 0.08 |

Table 8 shows the micromovement of a conventional non-fluted implant. The mean displacement is higher still than either the present invention or the conventional fluted implant.

TABLE 8

Micromovement of a Conventional Non-fluted Implant.

| Force ((N)) | Implant Number/Motion mm | | | | | | | | | | | | Mean Disp. (mm) | Std Dev |
|---|---|---|---|---|---|---|---|---|---|---|---|---|---|---|
| | 1 | 2 | 3 | 4 | 5 | 6 | 7 | 8 | 9 | 10 | 11 | 12 | | |
| 10 | 0.032 | 0.032 | 0.023 | 0.056 | 0.026 | 0.104 | 0.028 | 0.067 | 0.011 | 0.014 | 0.091 | 0.028 | 0.04 | 0.03 |
| 15 | 0.059 | 0.067 | 0.048 | 0.074 | 0.045 | 0.198 | 0.077 | 0.116 | 0.027 | 0.049 | 0.177 | 0.054 | 0.08 | 0.05 |
| 20 | 0.094 | 0.114 | 0.077 | 0.116 | 0.08 | 0.31 | 0.145 | 0.171 | 0.088 | 0.102 | 0.255 | 0.096 | 0.14 | 0.07 |
| 25 | 0.132 | 0.185 | 0.099 | 0.175 | 0.12 | 0.433 | 0.188 | 0.242 | 0.125 | 0.168 | 0.343 | 0.132 | 0.20 | 0.10 |
| 30 | 0.163 | 0.231 | 0.123 | 0.226 | 0.168 | 0.534 | 0.218 | 0.32 | 0.183 | 0.229 | 0.432 | 0.18 | 0.25 | 0.12 |
| 35 | 0.221 | 0.259 | 0.143 | 0.258 | 0.235 | 0.649 | 0.248 | 0.403 | 0.244 | 0.331 | 0.538 | 0.228 | 0.31 | 0.15 |
| 40 | 0.258 | 0.284 | 0.164 | 0.289 | 0.283 | 0.74 | 0.28 | 0.456 | 0.297 | 0.428 | 0.62 | 0.264 | 0.36 | 0.17 |
| 45 | 0.292 | 0.31 | 0.185 | 0.317 | 0.307 | 0.796 | 0.304 | 0.501 | 0.329 | 0.505 | 0.703 | 0.287 | 0.40 | 0.19 |
| 50 | 0.322 | 0.335 | 0.207 | 0.343 | 0.331 | 0.862 | 0.331 | 0.541 | 0.35 | 0.573 | 0.798 | 0.317 | 0.44 | 0.21 |
| 55 | 0.351 | 0.358 | 0.227 | 0.373 | 0.356 | 0.915 | 0.358 | 0.579 | 0.375 | 0.615 | 0.86 | 0.346 | 0.48 | 0.22 |
| 60 | 0.379 | 0.383 | 0.248 | 0.399 | 0.381 | 0.945 | 0.388 | 0.615 | 0.4 | 0.65 | 0.896 | 0.373 | 0.50 | 0.22 |
| 65 | 0.405 | 0.407 | 0.273 | 0.427 | 0.404 | 0.98 | 0.417 | 0.649 | 0.425 | 0.707 | 0.933 | 0.403 | 0.54 | 0.23 |
| 70 | 0.432 | 0.434 | 0.293 | 0.456 | 0.432 | 1.019 | 0.445 | 0.684 | 0.45 | 0.764 | 0.966 | 0.431 | 0.57 | 0.23 |
| 75 | 0.465 | 0.46 | 0.318 | 0.489 | 0.457 | 1.054 | 0.474 | 0.723 | 0.479 | 0.804 | 0.995 | 0.461 | 0.60 | 0.24 |
| 80 | 0.491 | 0.49 | 0.336 | 0.52 | 0.485 | 1.091 | 0.509 | 0.763 | 0.505 | 0.845 | 1.03 | 0.496 | 0.63 | 0.24 |
| 85 | 0.524 | 0.521 | 0.36 | 0.535 | 0.513 | 1.143 | 0.545 | 0.8 | 0.542 | 0.888 | 1.08 | 0.569 | 0.67 | 0.25 |
| 90 | 0.558 | 0.553 | 0.385 | 0.552 | 0.545 | 1.191 | 0.583 | 0.839 | 0.57 | 0.959 | 1.113 | 0.569 | 0.70 | 0.26 |
| 95 | 0.588 | 0.59 | 0.41 | 0.605 | 0.58 | 1.238 | 0.631 | 0.881 | 0.596 | 1.024 | 1.163 | 0.607 | 0.74 | 0.27 |
| 100 | 0.632 | 0.623 | 0.435 | 0.642 | 0.616 | 1 | 0.67 | 0.924 | 0.639 | 1.074 | 1.197 | 0.649 | 0.78 | 0.27 |

Figure 10:
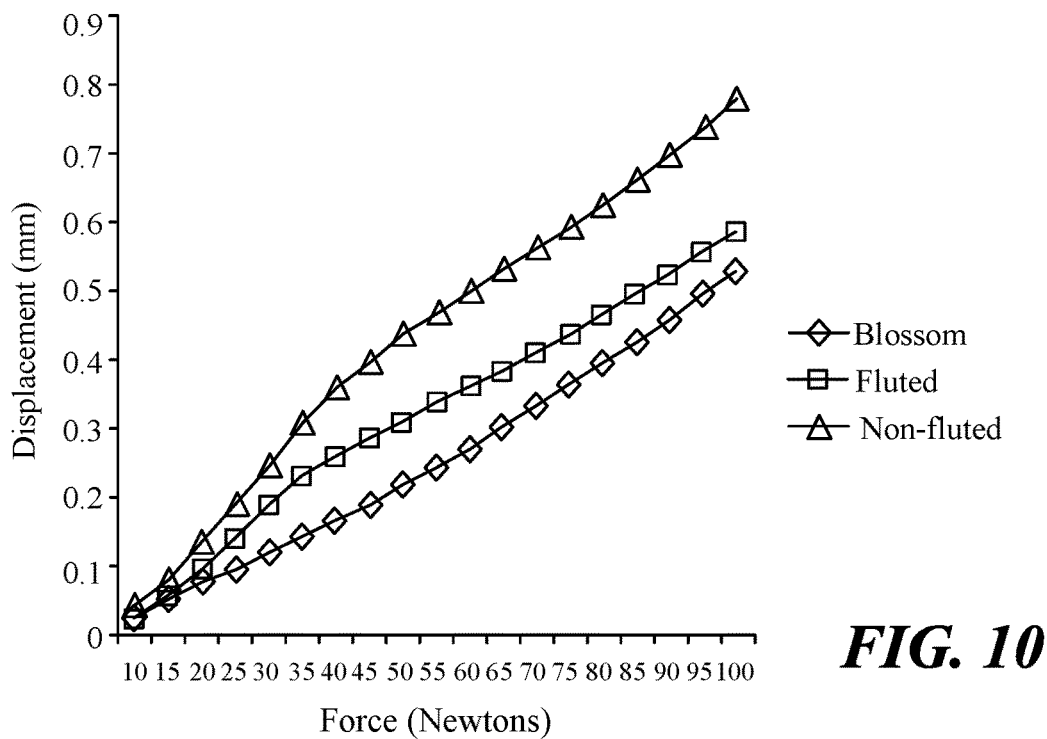
FIG. 10 is a composite line graph comparing the micro-movement of an implant of the present invention with conventional fluted and non-fluted implants.

FIG. 10 is a line graph of the mean displacement data from tables 7, 8 and 9. The reduction of micromotion is readily apparent in FIG. 10.

Figure 11:
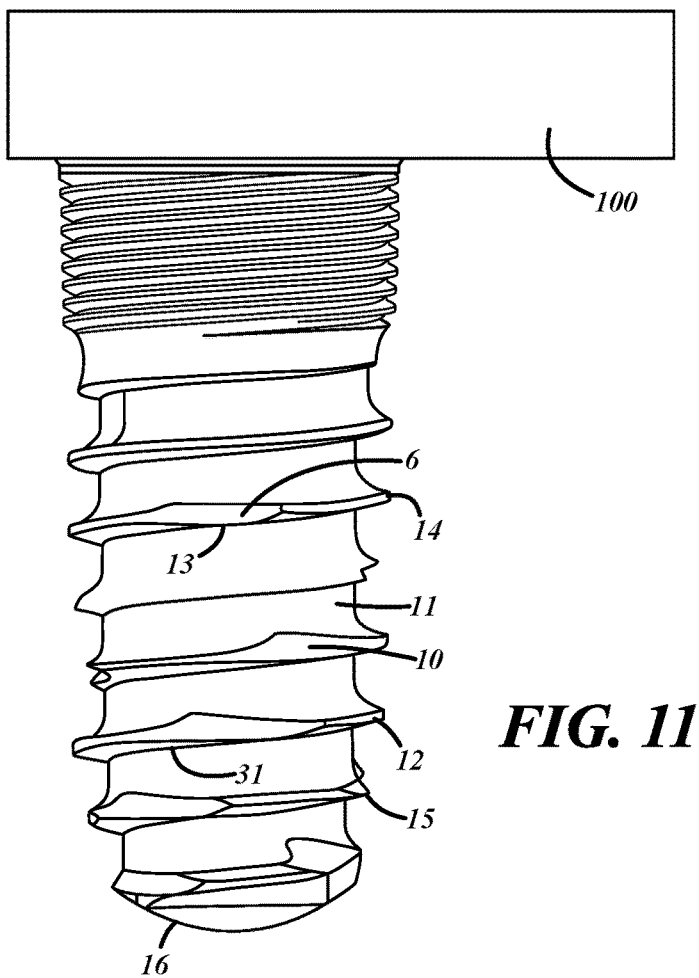
FIG. 11 is a drawing illustrating an osseointegrated implant for a hearing aid.

In yet another embodiment devices of the present invention, implants of the present invention can be used to support osseointegrated hearing aids. Osseointegrated hearing aids are those in which the sound is mechanically transmitted through bone. These aids include an implant which is inserted into the skull. A hearing aid transducer is affixed to the implant. Referring to FIGS. 1-3, an implant for a hearing aid can be constructed in the same manner as a dental implant taking into account the thickness of the skull where it will be implanted. The implant comprises a substantially cylindrical body 1 having a proximal end 2 and a distal end 3. The proximal end contains a prosthetic platform 7 onto which a the hearing aid 100 will be fitted. The body contains at least one external helical thread 9 which runs from the distal end 3 to the proximal end 2. The helical thread 9 may be right or left handed and contains at least one cutting edge 6 for each turn of the cutting head. The implant further comprises a second helix 10 running in the opposite direction of the helical thread from the distal end 3 to the proximal end 2. The second helix can be seen more clearly in FIG. 4 in which the helical thread 9 has been omitted for clarity. The hearing aid on the implant can be seen in FIG. 11.

Because the implant of the present invention requires a smaller pilot hole than conventional implants, the implant is more secure and will enable a hearing aid in many instances to be mounted immediately.

The implant of the present invention is used in a conventional manner. The surgeon will drill a pilot hole for the implant. The implant is attached to an insertion tool and turned into the pilot hole. Upon turning, the cutting edge 6 will cut a groove into the bone into which the helical thread 9 will follow. Because cutting edge 6 has a sharp edge leading into a narrow plateau on the helical thread 9, less bone debris is generated. This debris is pushed towards the proximal end of the body through the second helical groove 10. This movement of debris keeps the pilot hole relatively free from debris thereby preventing debris from filling the pilot hole or binding or jamming the implant. This reduces incidences of the implant prematurely bottoming out in the pilot hole because of debris filling the hole and reduces the debris caught in the helical groove thereby reducing friction on the cutting surfaces which reduces the torque required for insertion.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and cope of the invention as defined by the appended claims.

What is claimed is:

1. A method for installing a self-threading implant in bone, the method including the steps of:
   engaging a distal end of an implant against a bone;
   driving the implant into the bone by rotating the implant around a rotational axis of the implant and thus driving into the bone;
   a helical thread coaxially wound around at least a portion of a body of the implant, and
   a first blade formed in the thread and having an arcuate cutting edge that curves helically aft and radially outward from adjacent a minor thread diameter to merge with a thread ridge at a major thread diameter;
   generating bone debris as the implant is driven into the bone;
   distributing the generated bone debris across a body length of the implant by moving the generated bone debris in a direction, relative to the implant, that is rotationally in the direction of implant rotation and axially outward toward a proximal end of the implant, as the implant is driven into the bone.

2. The method of claim 1 in which the distributing step includes moving the generated bone debris outward and in the direction of implant rotation via a helical groove formed coaxially into the thread and having a handedness opposite that of the thread.

3. The method of claim 1 in which the step of driving the implant into bone includes passing into the bone a second blade formed in the thread and having an arcuate cutting edge that curves helically aft and radially outward from adjacent a minor thread diameter to merge with a thread ridge at a major thread diameter, a forward surface of the first blade being in helical alignment with a forward surface of the second blade, the helical alignment of the forward blade surfaces being in opposite handedness to the helical thread.

4. The method of claim 1 in which the step of moving the bone debris outward includes receiving the bone debris in a helical groove formed coaxially into the thread and having a handedness opposite that of the thread.

\* \* \* \* \*